(12) United States Patent
Banov et al.

(10) Patent No.: US 8,906,397 B2
(45) Date of Patent: *Dec. 9, 2014

(54) PERMEATION ENHANCERS FOR TOPICAL FORMULATIONS

(75) Inventors: Daniel Banov, Sugar Land, TX (US); August S. Bassani, Katy, TX (US)

(73) Assignee: Professional Compounding Centers of America, Ltd, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/547,813

(22) Filed: Jul. 12, 2012

(65) Prior Publication Data

US 2012/0277195 A1    Nov. 1, 2012

Related U.S. Application Data

(63) Continuation-in-part of application No. 13/022,361, filed on Feb. 7, 2011, and a continuation-in-part of application No. 13/022,385, filed on Feb. 7, 2011.

(51) Int. Cl.

| *A61K 8/02* | (2006.01) |
|---|---|
| *A61K 9/06* | (2006.01) |
| *A61K 31/192* | (2006.01) |
| *A61K 9/00* | (2006.01) |
| *A61K 47/44* | (2006.01) |
| *A61K 36/889* | (2006.01) |
| *A61K 36/48* | (2006.01) |

(52) U.S. Cl.
CPC ............ *A61K 9/06* (2013.01); *A61K 31/192* (2013.01); *A61K 9/0014* (2013.01); *A61K 47/44* (2013.01); *A61K 36/889* (2013.01); *A61K 36/48* (2013.01)
USPC ........................................... 424/401

(58) Field of Classification Search
None
See application file for complete search history.

(56) References Cited

U.S. PATENT DOCUMENTS

| 5,238,933 | A | 8/1993 | Catz et al. |
|---|---|---|---|
| 5,505,960 | A | 4/1996 | Lucchetti et al. |
| 5,702,694 | A * | 12/1997 | Chamness ................ 424/78.03 |
| 6,979,461 | B1 | 12/2005 | Ohtomo et al. |
| 2003/0017183 | A1 | 1/2003 | Pollock |
| 2005/0281749 | A1 | 12/2005 | Willcox et al. |
| 2007/0082042 | A1 | 4/2007 | Park et al. |
| 2007/0264221 | A1 | 11/2007 | Moser et al. |
| 2008/0097607 | A1 | 4/2008 | Bakkar et al. |
| 2008/0152681 | A1 | 6/2008 | Brown et al. |
| 2008/0193511 | A1 | 8/2008 | Massing |
| 2009/0196895 | A1 | 8/2009 | Golz-Berner et al. |
| 2009/0285876 | A1 * | 11/2009 | Hein et al. ................ 424/443 |
| 2011/0027327 | A1 | 2/2011 | Albrecht |
| 2011/0274630 | A1 * | 11/2011 | Fenyvesi et al. ............. 424/58 |

OTHER PUBLICATIONS

BIO Nat Consult Pracaxi oil.*
PreInterview First Action Interview in U.S. Appl. No. 13/022,361 mailed Sep. 5, 2012.
First Action Interview Office Action in U.S. Appl. No. 13/022,361, mailed Jan. 3, 2013.
Preinterview First Action Interview in U.S. Appl. No. 13/022,385 mailed May 24, 2013.
Final Office Action in U.S. Appl. No. 13/022,361, mailed Jul. 2, 2013.
PCT/US App. No. 12/23993 Search Report and Written Opinion dated May 23, 2012.
Non-Final Office Action mailed Aug. 23, 2013 in U.S. Appl. No. 13/022,385.
Final Office Action in U.S. Appl No. 13/022,385, mailed Mar. 10, 2014.
International Preliminary Report on Patentability dated Aug. 13, 2013 in PCTUS2012023992, 6 pages.
International Preliminary Report on Patentability dated Aug. 13, 2013 in PCTUS2012023993, 5 pages.
Notice of Allowance dated Jul. 21, 2014 in U.S. Appl. No. 13/022,361, 9 pages.

* cited by examiner

*Primary Examiner* — Snigdha Maewall
(74) *Attorney, Agent, or Firm* — Shook, Hardy & Bacon LLP

(57) ABSTRACT

A composition to be used as a permeation enhancer is provided. The composition may be added to topical cosmetics or pharmaceutical formulations that are topically applied. The composition comprises about 10-50% of Pracaxi oil, 15-40% of Patauá oil, 10-30% of Inaja oil, and 10-30% of one or more emollients.

12 Claims, 4 Drawing Sheets

US 8,906,397 B2

PERMEATION ENHANCERS FOR TOPICAL FORMULATIONS

CROSS-REFERENCE TO RELATED APPLICATIONS

This application is a continuation-in-part to U.S. application Ser. No. 13/022,361, filed Feb. 7, 2011, entitled "PERMEATION ENHANCERS FOR TOPICAL FORMULATIONS," and is also a continuation-in-part to U.S. application Ser. No. 13/022,385, filed Feb. 7, 2011, entitled "PERMEATION ENHANCERS WITH LIPOSOMES FOR TOPICAL FORMULATIONS," both of which are herein incorporated by reference in their entirety.

STATEMENT REGARDING FEDERALLY SPONSORED RESEARCH OR DEVELOPMENT

Not applicable.

BACKGROUND

Typically, active ingredients, such as drugs, are not easily permeated through the skin when used in topical cosmetic products or pharmaceutical formulations that are topically delivered. Further, some active ingredients may need to be pre-encapsulated. Additionally, while acids such as behenic acid and oleic acid have traditionally been added to topical formulations to assist with the delivery of drugs through the skin, these acids can be extremely irritating to the skin when used alone. In addition to high levels of irritancy, formulations typically used to enhance permeation through the skin can be unstable.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter. Embodiments of the present invention are directed to a composition that enhances permeation of an active ingredient, such as a drug, through the skin. The composition may be used with, for example, topical cosmetics or pharmaceutical formulations that are topically applied. Methods of preparing such a composition are also described herein.

In one embodiment, a natural composition to be used for skin permeation is provided. The natural composition includes a combination of A natural composition to be used for skin permeation, the composition comprising a combination of 10-50% w/w of Pracaxi oil, 15-40% w/w of Patauá oil, 10-30% w/w of Inaja oil, and 10-30% w/w of one or more emollients.

In another embodiment, a composition to be used for skin permeation is provided. The composition includes a combination of 1-20% w/w of Pracaxi oil, 10-40% w/w of one or more phospholipids, 5-20% w/w of one or more of Patauá oil or Inaja oil, and 5-30% w/w of one or more emulsifiers In yet another embodiment, a method for preparing a natural composition to be used for skin permeation. The method includes combining one or more phospholipids, Pracaxi oil, one or more of Patauá oil or Inaja oil, and one or more emulsifiers. The method further includes dispersing the composition using a high shear homogenizer, and creating negative pressure in a vessel that has the composition.

Additional aspects of the invention, together with the advantages and novel features appurtenant thereto, will be set forth in part in the description that follows, and in part will become apparent to those skilled in the art upon examination of the following, or may be learned from the practice of the invention. The objects and advantages of the invention may be realized and attained by means, instrumentalities, and combinations particular pointed out in the appended claims.

BRIEF DESCRIPTION OF THE SEVERAL VIEWS OF THE DRAWINGS

Illustrative embodiments of the present invention are described in detail below with reference to the attached drawing figures, and wherein.

DETAILED DESCRIPTION

Figure 1:
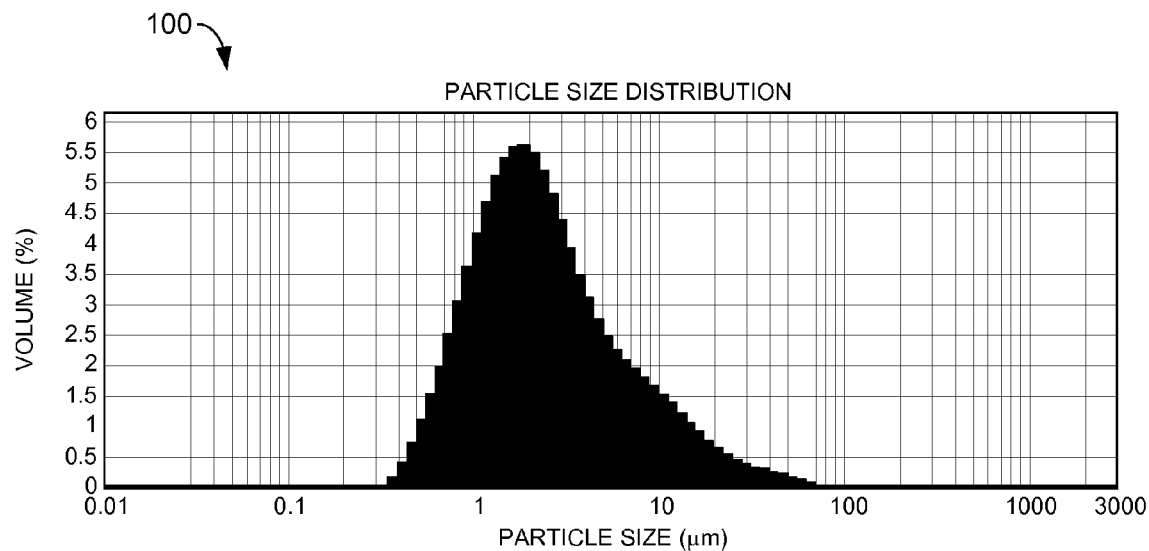
FIG. 1 is a logarithmic graph illustrating particle size distribution, in accordance with an embodiment of the present invention.

Embodiments of the present invention are directed to a composition of ingredients that, in one embodiment is a natural composition or formulation. The composition contains one or more naturally occurring substances, including one or more phospholipids, one or more oils rich in essential fatty acids, behenic acid, and oleic acid, one or more skin lipids, and one or more butters rich in linoleic acid and linolenic acid. This composition, in one embodiment, is used as a penetration enhancer for a number of different compounds, including topical cosmetics and pharmaceutical formulations. While the composition is safe and effective, it is comprised of natural ingredients that assist with penetration of an active ingredient through the skin.

The fatty acid microparticle composition described herein contains, among other components, behenic acid, oleic acid, omega-3 fatty acids, and phospholipids. This composition may be produced under highly controlled production conditions using methods described herein, such as by using a high shear homogenizer, which results in a relatively uniform size distribution. For instance, in embodiments, the size of the particles is around 5-20 microns, which increases skin permeation of an active ingredient through synergism of all of the components. The composition is generally used for administering active ingredients through the skin, in addition to hydrating the skin by forming a semi-occlusive film on the skin by way of the unique mixture of ingredients.

The composition described herein may be formulated as a liquid or a semi-liquid, and as mentioned, acts as a penetration enhancer for active ingredients contained within a final product. The effect of the penetration enhancing composition, as described herein, occurs because of its presence in the final formulation. This eliminates the need for pre-encapsulation of the active ingredients. Additionally, this composition may be used at the pharmacy level, whereby a pharmacist would be able to add the composition to a cream or other topical formulation, at a certain percentage, thus providing penetration power to the topical formulation. This composition used for penetration enhancement is designed to be useable in a large variety of topical systems, with decreased concern for the stability and aesthetic properties of the final formulation.

While there is no official legal definition of the term "natural" as it relates to cosmetic ingredients, Ecocert, BDIH (the Federation of German Industries and Trading) and the Soil Association both agree that the term implies a ban on the use of petrochemical derived ingredients, silicones, ethoxylated raw materials, and halogen organic compounds.

As mentioned, the composition described herein contains one or more naturally occurring substances, including one or more phospholipids, one or more oils rich in essential fatty acids, behenic acid, and oleic acid, one or more skin lipids, and one or more butters rich in linoleic acid and linolenic acid. These ingredients, together, act synergistically to increase the skin permeation of water and oil soluble products. The composition, which is a solution, may be added to a gel or emulsion at a given percent to give permeation power to the otherwise topical preparation. When the composition described herein is prepared, liposomes are formed from the fatty acids, including behenic acid and oleic acid that are present the one or more oils, and are stabilized by the phospholipids in the composition. More specifically, when the permeation enhancer composition described herein is added to water or a water-containing composition, liposomes are formed. In alternative embodiment of the present invention, lauric acid, in addition to behenic acid and oleic acid is used, as lauric acid also helps to deliver active ingredients transdermally, or through the skin.

Liposomes are artificially prepared vesicles made of lipid bilayer, and have concentric phospholipid bilayers. In some embodiments, liposomes are filled with drugs or other active ingredients and used to deliver these drugs. Liposomes may be composed of naturally-derived phospholipids with mixed lipid chains or other surfactants. In embodiments of the present invention, the liposomes that are formed are used to deliver drugs or other active ingredients topically to the skin's surface. The liposomes that are formed using embodiments of the present invention are stabilized by the phospholipids, in addition to their small and relatively uniform particle size, as described in more detail herein. Various molecules from those having a low molecular weight, such as glucose, to those having a high molecular weight, such as peptides and proteins, may be incorporated in liposomes. As mentioned water soluble compounds/drugs are present in aqueous compartments while lipid soluble compounds/drugs and amphiphilic compounds/drugs insert themselves in phospholipid bilayers. The liposomes containing drugs may be administered by various routes, including intravenous, oral inhalation, local application, ocular, etc. Because of this, liposomes can be used for the treatment of many diseases.

Typically, multilamellar liposomes (MLV) range from 500 to 10,000 nm, while unilamellar liposomes may be small (SUV) or large (LUV). SUV liposomes are typically smaller than 50 nm, while LUV liposomes are usually larger than 50 nm. Liposomes that are very large are called giant liposomes, whose size may range from 10,000 to 100,000 nm These may be either unilamellar or multilamellar. The liposomes containing encapsulated vesicles are called multi-vesicular, and their size may range from 2,000 to 40,000 nm. An exemplary technique of microfluidization/microemulsification/homogenization for the large scale manufacture of liposomes is by recycling the sample to reduce the size range. This process is reproducible and yields liposomes with good aqueous phase encapsulation.

Additionally, due to their amphiphilic character, liposomes are a powerful solubilizing system for a wide range of compounds. In addition to these physico-chemical properties, liposomes exhibit many special biological characteristics, including specific interactions with biological membranes and various cells. These properties point to several possible applications with liposomes as the solubilizers for difficult-to-dissolve substances, dispersants, sustained release systems, delivery systems for the encapsulated substances, stabilizers, protective agents, microencapsulation systems and microreactors, to name just a few. Liposomes can be made entirely from naturally occurring substances and are therefore nontoxic, biodegradable and non immunogenic.

The industrial applications include liposomes as drug delivery vehicles in medicine, adjuvants in vaccination, signal enhancers/carriers in medical diagnostics and analytical biochemistry, solubilizers for various ingredients, as well as support matrix for various ingredients and penetration enhancer in cosmetics.

Phospholipids, generally, are lipids that contain one or more phosphate groups. Phospholipids are fatlike organic compounds that resemble triglycerides, but have a fatty acid with a phosphate-containing polar group. The polar end of the molecule is hydrophilic, or soluble in water, and the other end, or the fatty-acid end is hydrophobic, or soluble in fats. Phospholipids are ideal compounds for forming the biological membrane. There are two recognized classes of phospholipids, including phosphoglycerids, or those that have a glycerol backbone, and those phospholipids that contain sphingosine. The most abundant types of phosphoglycerids are phosphatidylcholine (lecithin), phosphatidylethanolamine, phosphatidylserine, phosphatidylinositol, phosphatidylglycerol, and cardiolipin.

Many types of phospholipids may be used in embodiments of the present invention. In one embodiment, the phospholipids used in the composition include one or more of phosphatidylcholine, lysophosphotidylcholine, hydrogenated phospholipids, and unsaturated phospholipids. As mentioned, there are two categories of phospholipids. Examples of phosphoglycerids include phosphatidic acid (phosphatidate) (PA), phosphatidylethanolamine (cephalin) (PE), phosphatidylcholine (lecithin) (PC), Phosphatidylserine (PS), and Phosphoinositides, which further include phosphatidylinositol (PI), phosphatidylinositol phosphate (PIP), phosphatidylinositol bisphosphate (PIP2), and phosphatidylinositol triphosphate (PIP3). Phospholipids that contain sphingosine, also termed phosphosphingolipids, include ceramide phosphorylcholine (sphingomyelin) (SPH), ceramide phosphorylethanolamine (sphingomyelin) (Cer-PE), and ceramide phosphorylglycereol. The term lysophospholipids' (LPL) refers to any phospholipid that is missing one of its two O-acyl chains. Thus, LPLs have a free alcohol in either the sn-1 or sn-2 position. The prefix 'lyso-' comes from the fact that lysophospholipids were originally found to be hemolytic, but is now used to refer generally to phospholipids missing an acyl chain. LPLs are usually the result of phospholipase A-type enzymatic activity on regular phospholipids, such as phosphatidylcholine or phosphatidic acid, although they can also be formed by the acylation of glycerophospholipids or the phosphorylation of monoacylglycerols.

For exemplary purposes only, lysophosphatidylcholine (LPC) has been found to penetrate into the dermis faster than phosphatidylcholine, such that a small amount of LPC can penetrate the skin without damaging skin structure, and is enzymatically degraded into several lipids. LPC has bactericidal and antiviral activity, and as such is a useful agent for dermatological use. LPC also does not damage the structure of the skin. Even further, LPC has been found to have a positive effect on the basement membrane, as it stimulates the synthesis of Laminin 5, a factor supporting the regeneration of an aging basement membrane. Lysophospholipids (LP), such as lysophosphatidic acid and sphingosine 1-phosphate are membrane-derived bioactive lipid mediators. LPs can effect fundamental cellular functions, which include proliferation, differentiation, survival, migration, adhesion, invasion, and morphogenesis. These functions influence many biological processes that include neurogenesis, angiogenesis, wound healing, immunity, and carcinogenesis.

Phospholipids may further include 1,2-Didecanoyl-sn-glycero-3-phosphocholine (Phosphatidylcholine), 1,2-Dierucoyl-sn-glycero-3-phosphate (Sodium Salt) (Phosphatidic acid), 1,2-Dierucoyl-sn-glycero-3-phosphocholine (Phosphatidylcholine), 1,2-Dierucoyl-sn-glycero-3-phosphoethanolamine (Phosphatidylethanolamine), 1,2-Dierucoyl-sn-glycero-3[Phospho-rac-(1-glycerol . . . ) (Sodium Salt) (Phosphatidylglycerol), 1,2-Dilinoleoyl-sn-glycero-3-phosphocholine (Phosphatidylcholine), 1,2-Dilauroyl-sn-glycero-3-phosphate (Sodium Salt) (Phosphatidic acid), 1,2-Dilauroyl-sn-glycero-3-phosphocholine (Phosphatidylcholine), 1,2-Dilauroyl-sn-glycero-3-phosphoethanolamine (Phosphatidylethanolamine), 1,2-Dilauroyl-sn-glycero-3[Phospho-rac-(1-glycerol . . . ) (Sodium Salt) (Phosphatidylglycerol), 1,2-Dilauroyl-sn-glycero-3 [Phospho-rac-(1-glycerol . . . ) (Ammonium Salt) (Phosphatidylglycerol), 1,2-Dilauroyl-sn-glycero-3-phosphoserine (Sodium Salt) (Phosphatidylserine), 1,2-Dimyristoyl-sn-glycero-3-phosphate (Sodium Salt) (Phosphatidic acid), 1,2-Dimyristoyl-sn-glycero-3-phosphocholine (Phosphatidylcholine), 1,2-Dimyristoyl-sn-glycero-3-phosphoethanolamine (Phosphatidylethanolamine), 1,2-Dimyristoyl-sn-glycero-3[Phospho-rac-(1-glycerol . . . ) (Sodium Salt) (Phosphatidylglycerol), 1,2-Dimyristoyl-sn-glycero-3[Phospho-rac-(1-glycerol . . . ) (Ammonium Salt) (Phosphatidylglycerol), 1,2-Dimyristoyl-sn-glycero-3[Phospho-rac-(1-glycerol . . . ) (Sodium/Ammonium Salt) (Phosphatidylglycerol), 1,2-Dimyristoyl-sn-glycero-3-phosphoserine (Sodium Salt) (Phosphatidylserine), 1,2-Dioleoyl-sn-glycero-3-phosphate (Sodium Salt) (Phosphatidic acid), 1,2-Dioleoyl-sn-glycero-3-phosphocholine (Phosphatidylcholine), 1,2-Dioleoyl-sn-glycero-3-phosphoethanolamine (Phosphatidylethanolamine), 1,2-Dioleoyl-sn-glycero-3 [Phospho-rac-(1-glycerol . . . ) (Sodium Salt) (Phosphatidylglycerol), 1,2-Dioleoyl-sn-glycero-3-phosphoserine (Sodium Salt) (Phosphatidylserine), 1,2-Dipalmitoyl-sn-glycero-3-phosphate (Sodium Salt) (Phosphatidic acid), 1,2-Dipalmitoyl-sn-glycero-3-phosphocholine (Phosphatidylcholine), 1,2-Dipalmitoyl-sn-glycero-3-phosphoethanolamine (Phosphatidylethanolamine), 1,2-Dipalmitoyl-sn-glycero-3[Phospho-rac-(1-glycerol . . . ) (Sodium Salt) (Phosphatidylglycerol), 1,2-Dipalmitoyl-sn-glycero-3[Phospho-rac-(1-glycerol . . . ) (Ammonium Salt) (Phosphatidylglycerol), 1,2-Dipalmitoyl-sn-glycero-3-phosphoserine (Sodium Salt) (Phosphatidylserine), 1,2-Distearoyl-sn-glycero-3-phosphate (Sodium Salt) (Phosphatidic acid), 1,2-Distearoyl-sn-glycero-3-phosphocholine (Phosphatidylcholine), 1,2-Distearoyl-sn-glycero-3-phosphoethanolamine (Phosphatidylethanolamine), 1,2-Distearoyl-sn-glycero-3[Phospho-rac-(1-glycerol . . . ) (Sodium Salt) (Phosphatidylglycerol), 1,2-Distearoyl-sn-glycero-3 [Phospho-rac-(1-glycerol . . . ) (Ammonium Salt) (Phosphatidylglycerol), 1,2-Distearoyl-sn-glycero-3-phosphoserine (Sodium Salt) (Phosphatidylserine), Egg-PC (Phosphatidylcholine), Hydrogenated Egg PC (Phosphatidylcholine), High purity Hydrogenated Soy PC (Phosphatidylcholine), Hydrogenated Soy PC (Phosphatidylcholine), 1-Myristoyl-sn-glycero-3-phosphocholine (Lysophosphatidylcholine), 1-Palmitoyl-sn-glycero-3-phosphocholine (Lysophosphatidylcholine), 1-Stearoyl-sn-glycero-3-phosphocholine (Lysophosphatidylcholine), 1-Myristoyl-2-palmitoyl-sn-glycero 3-phosphocholine (Phosphatidylcholine), 1-Myristoyl-2-stearoyl-sn-glycero-3-phosphocholine (Phosphatidylcholine), 1-Palmitoyl-2-myristoyl-sn-glycero-3-phosphocholine (Phosphatidylcholine), 1-Palmitoyl-2-oleoyl-sn-glycero-3-phosphocholine (Phosphatidylcholine), 1-Palmitoyl-2-oleoyl-sn-glycero-3-phosphoethanolamine (Phosphatidylethanolamine), 1-Palmitoyl-2-oleoyl-sn-glycero-3[Phospho-rac-(1-glycerol) . . . ] (Sodium Salt) (Phosphatidylglycerol), 1-Palmitoyl-2-stearoyl-sn-glycero-3-phosphocholine (Phosphatidylcholine), 1-Stearoyl-2-myristoyl-sn-glycero-3-phosphocholine (Phosphatidylcholine), 1-Stearoyl-2-oleoyl-sn-glycero-3-phosphocholine (Phosphatidylcholine), and 1-Stearoyl-2-palmitoyl-sn-glycero-3-phosphocholine (Phosphatidylcholine). These examples of phospholipids are provided for exemplary purposes only, and other phospholipids not specifically mentioned herein are contemplated to be included in embodiments of the present invention.

Another component present in the composition described herein is oils that are rich sources of essential fatty acids, behenic acid, oleic acid, and in some instances, lauric acid. During life, skin is subjected to different perturbations (e.g., puberty, pregnancy, menopause, disease) and aggressions (e.g., UV, pollution, cold, detergent). These upheavals and external aggressions induce a decrease of membrane fluidity involving a disruption of the lipidic barrier (e.g., cutaneous dryness and roughness) and a loss of the epidermic elasticity (e.g., formation of irregularities, stretch marks, and furrows). All of these events induce a cutaneous dehydration accompanied by the appearance of squamas and wrinkles on the skin's surface. The supply of essential fatty acids and antioxidant molecules can restore the cutaneous permeability and the function of the skin barrier. They also contribute to the control of the imperceptible water loss and maintain moisture of the skin.

Behenic acid, oleic acid, and lauric acid, when used by themselves, may be irritating when applied to the skin, which makes them difficult to use as permeation enhancers. While having an irritating effect on the skin, these acids are also effective vehicles at delivering drugs through the skin. In one embodiment, an oil from a tree in Brazil has the highest natural sources of behenic acid and oleic acid. The tree is called *Pentaclethara Macroloba*, or more commonly termed the Pracaxi tree. *Pentaclethra Macroloba* seed oil, also called Pracaxi oil, is extracted from the tree, and as mentioned, contains high concentrations of behenic acid and oleic acid. Pracaxi oil has been used by people living near the Amazon river as an antioxidant, and has been thought to have antifungal and antibacterial properties. Further, Pracaxi oil has been widely used to treat snake bites and aid in the healing of ulcers. Pracaxi oil, however, has not been used as a permeation enhancer. Typically, Pracaxi oil contains about 20% behenic acid and about 35% oleic acid. In some cases, it may contain more than these percentages. As the behemic acid and oleic acid are present in an oil, the effects of the acids are less irritating on the skin, and as such makes the oil a good choice for one of the ingredients of a penetration enhancer.

The fatty acid composition of Pracaxi oil is illustrated below in Table 1.

TABLE 1

Fatty Acid Composition of Pracaxi Oil
Fatty Acid Composition of Pracaxi Oil

| Fatty Acids | Carbon Atoms | Composition % |
| --- | --- | --- |
| Lauric | 12:00 | 1.30 |
| Myristic | 14:00 | 1.21 |
| Palmitic | 16:00 | 2.04 |
| Stearic | 18:00 | 2.14 |
| Oleic | 18:10 | 44.32 |
| Linoleic | 18:20 | 1.96 |
| Linolenic | 18:30 | 2.30 |
| Behenic | 22:00 | 19.67 |
| Lignoceric | 24:00 | 14.81 |

Another oil that may be used in some embodiments in combination with Pracaxi oil is *Plukenetia Volubilis* seed oil, also known as Inca Inchi. This oil is native to the Amazon Rainforest. The seeds of Inchi are high in protein (around 27%) and oil (around 35-60%) content. This oil extracted from the *Plukenetia volubilis* plant is one of the largest plant sources of the Omega family of fatty acids, including a high concentration of protein. The oil is also rich in iodine and vitamin A and vitamin E. This is a natural oil with an exceptional content in polyunsaturated fatty acids (greater than 90%) and tocopherols (1.5 to 2 g/kg). It is a vegetable oil having both essential fatty acids in such a high amount, including 49% of alphalinolenic acid (omega-3) and 34% of linoleic acid (omega-6). While Plukenetia Volubilis seed oil has a very high amount of fatty acids, it also has high amounts of behenic acid (10-30%) and oleic acid (35-80%).

Still yet another oil that may be used is from a tree called *Maximiliana Maripa palm*, or Inaja. Inaja has one of the highest sources of lauric acid (greater than 40%) and oleic acid (greater than 15%). Further, the highest concentration of fatty acids found in the Inaja is found in the kernal oil, as opposed to the pulp oil. Inaja is an indigenous Amazonian palm widespread in the state of Pará, growing around the Amazon River estuary. Oil from Inaja is extracted from the fruits of the Inaja palm, which is comprised of about 70% short-chain fatty acids, including lauric acid and myristic acid. This palm has been used in the production of bar soap because of its high concentration of lauric acid. The fatty acid composition of Inaja kernel oil is shown in Table 2 below.

TABLE 2

Fatty Acid Composition of Inaja Kernel Oil

| Fatty Acids | Carbon Atoms | Composition % |
| --- | --- | --- |
| Lauric | 12:00 | 40.5 |
| Myristic | 14:00 | 25 |
| Palmitic | 16:00 | 9 |
| Stearic | 18:00 | 2.4 |
| Oleic | 18:10 | 10.8 |
| Linoleic | 18:20 | 1.96 |
| Linolenic | 18:30 | 2.4 |
| Behenic | 22:00 | trace |
| Lignoceric | 24:00 | trace |

As mentioned, behenic acid, lauric acid, oleic acid, and other fatty acids, when used by themselves, can be very rough on a person's skin. But, when an oil such as Plukenetia Volubilis seed oil and/or Pracaxi oil and/or Inaja oil are used, they work to enhance the restoration of cutaneous barrier organization and epidermal elasticity, in addition to contributing to the control of imperceptible water loss, thus maintaining skin hydration. This is, at least in part, due to the high amounts of essential fatty acids in these oils. The link between skin permeation and hydration is clear. Increasing the permeability of the stratum corneum may be achieved by the increase of water content in this tissue. Hydration by occlusion may cause a swelling of the corneocytes and subsequently may increase the skin permeation of actives. Here, the utilization of physiological lipids, essential fatty acids, and phospholipids provide penetration power with restorative benefits to the skin. While *Plukenetia Volubilis* seed oil, Pracaxi oil, and Inaja oil have been mentioned herein, other oils may also be used in alternative compositions, including, but not limited to, Buriti oil, Patauá, Tucuma, Bacuri, Ucuuba, Muru-Muru, and Copaiba.

Patauá oil is extracted from the mesocarp of the patauá palm and generally appears as a greenish-yellow and transparent liquid, with little odor and taste, having the physical appearance and composition of fatty acids that are similar to olive oil (*Olea europaea*). Its high content of unsaturated fatty acids is remarkable. Due to its high content of oleic acid, patauá oil has moisturizing properties, and can be used to care for skin and hair or in formulas to treat dandruff or to revitalize hair, and can also be used in soaps and moisturizers. The dry mesocarp of patauá contains about 7.4% protein and posses an excellent amino acid composition. Because of this, the protein of patauá is one of the most valuable found among plants and can be compared with the meat or milk from cattle. The most abundant sterols were $\Delta^5$avenosterol and β-sitosterol, with relative contents of 35 and 38%, respectively. The most abundant aliphatic alcohols were those with 7, 8 and 10 carbon atoms. Among tocopherols, α-tocopherol was predominant. Aldehydes such as heptanal, octanal and decanal were present in the volatile fraction along with terpenoid compounds. In general, this oil has a great potential due to the increasing use of lower quality edible oils for the production of biodiesel.

The fatty acid composition of Patauá oil can be found below in Table 3.

TABLE 3

Fatty Acid Composition of Patauá Oil
Fatty Acid Composition of SEJE (Patua Oil)

| Fatty Acids | Carbon Atoms | Composition % |
| --- | --- | --- |
| Palmitic | 16:00 | 13.2 |
| Palmitoleic | 16:10 | — |
| Stearic | 18:00 | 3.6 |
| Oleic | 18:10 | 77.7 |
| Linoleic | 18:20 | 2.7 |
| Linolenic | 18:30 | 0.6 |
| Arachidic | 20:00 | 2 |
| unsaturated | | 81.6 |

Another component of the composition described herein is skin lipids. Skin lipids, as used herein, are those lipids that are present at the skin's surface. Examples of skin lipids that may be used in the composition described herein include ceramides and/or squalene. Ceramides are the major lipid constituent of lamellar sheets Ceramides are a structurally heterogeneous and complex group of sphingolipids containing derivatives of sphingosine bases in amide linkage with a variety of fatty acids. Differences in chain length, type, and extent of hydroxylation and saturation are responsible for the heterogeneity of the epidermal sphingolipids. Ceramides play an important role in structuring and maintaining the water permeability barrier function of the skin. In conjunction with the other stratum corneum lipids, they form ordered structures. A structured semi-occlusive barrier that increases skin hydration is a positive influence on the penetration of active ingredients.

Another skin lipid that may be used is squalene, which is a lipid fat in the skin. When used together with a ceramide and a phospholipid, such as phosphatidylcholine, the formulation is mild such that is can be used on even sensitive skin. Squalene also helps to decrease water evaporation, thus speeding up skin permeation of actives and decreasing irritation made by surfactants found in emulsions. Squalene, being a natural emollient, imparts an elegant feel to formulations in which it is used. It is excellent for use in skin care and helps skin to retain moisture and feel soft and conditioned without feeling greasy.

Yet another component of the composition described herein is butters rich in linoleic acid and linolenic acid. One example of this type of butter is *butyrospermum parkii* butter, also known as shea butter. Other exemplary butters that may be used in embodiments of the present invention include, but are not limited to, cupuacu butter, buriti butter, passionfruit butter, mango butter, tucuma butter, palm butter, murumu butter, chamomile butter, cocoa butter, orange butter, lemon grass butter, avocado butter, tamanu butter, aloe butter, shea butter, monoi butter, pomegranate butter, almond butter, jojoba butter, red palm butter, acai butter, olive butter, matcha green tea butter, brazil nut butter, macadamia butter, kokum butter, mafura butter, coffee butter, tucuma butter, ucuuba butter, bacuri butter, and chamomile butter.

In embodiments of the present invention, the use of behenic acid, oleic acid, phospholipids, and the omega family enhance the permeation of drugs or other active ingredients through the skin in-vitro and in-vivo.

As mentioned, the composition described herein is produced such that the size of the particles is in the range of 5-20 microns, which provides a more stable vesicle than if the particle sizes were larger. Various methods may be used to produce particle sizes of about 5-20 microns. In one embodiment, a high pressure homogenizer is used. Using a high pressure homogenizer, the composition would be put under extreme pressure and forced through a very small opening. It is cycled through a number of times to achieve the desired particle size. But preferably, a high shear homogenizer is used in embodiments of the present invention, such as a high shear rotor-stator homogenizer under negative pressure. In one embodiment, an IKA Master Plant homogenizer is used, which can achieve RPMs over 8,000. Using this preferred method, the desired particle size is achieved without the use of a high pressure homogenizer, which is generally more expensive to use than the high shear homogenizer.

While concentrations of the components described herein may vary, Table 4 below illustrates exemplary concentrations, including the four main components described above, a concentration range, and optimal concentrations for each of the four components.

TABLE 4

Exemplary Concentrations of the Components

| Ingredients | Range concentration | Optimal concentration |
| --- | --- | --- |
| Phospholipids | 0.05-5% | 2% |
| Oils | 1-20% | 3% |
| Skin Lipids | 0.1-3% | 0.5% |
| Butters | 1-10% | 2% |

In one embodiment, the formulation contains about:

5-40% w/w Phosal 75 SA (alcohol; purified phosphatidylcholine; safflower oil; glyceryl stearate; coconut oil, ascorbyl palmitate);

5-40% w/w DMS 3015 (water, alcohol, caprylic/capric triglyceride, hydrogenated lecithin, butyrospermum parkii butter, squalene, and ceramide 3);

5-20% w/w Lipactive Inca Inchi (plukenetia volubilis seed oil, tocopherol);

5-40% w/w Pracaxi oil; and 10-90% w/w Purified water.

In an alternative embodiment where Inaja oil is used, an exemplary formulation contains about the concentration ranges shown below in Table 5.

TABLE 5

Ingredients of an Exemplary Composition

| Raw Material/Trade Name | International Nomenclature of Cosmetic Ingredients (INCI) Name | Optimal Concentration | Range Concentration |
| --- | --- | --- | --- |
| Vitamin E Acetate (DL) USP Liquid (1 IU/mg) | Tocopheryl Acetate | 1% | 0.1-5% |
| Pracaxi Oil | *Pentaclethra Macroloba* Seed Oil | 10% | 1-20% |
| Phosal 53 MCT | Alcohol & Ascorbyl Palmitate & Glyceryl Stearate & Lecithin & Caprylic/Capric Triglyceride & Oleic Acid & Tocopherol | 36% | 10-40% |
| Patauá Oil or Inaja Oil | *Oenocarpus Bataua* Fruit Oil | 14% | 5 to 20% |
| Labrasol | PEG-8 Caprylic/Capric Glycerides | 15% | 5 to 20% |
| Ceraphyl 230 | Diisopropyl Adipate | 24% | 10 to 30% |

In the embodiment above, the ingredients may be mixed at about 50 degrees Celsius until there is a uniform consistency. The mixture is then homogenized to reduce particle sizes by way of a rotor stator or high pressure homogenization, as further described herein. This composition listed in Table 5 above includes lecithin, which is a phospholipid. The exemplary formulation, however, does not include any butter or skin lipids, as is included in other formulations listed herein. The Ceraphyl 230 (Diisopropyl Adipate, a Monohydric Alcohol Di/Tri Esters) is an emollient and solvent with fast absorbency for creams and lotions. Diisopropyl Adipate ester is an excellent solvent and non-volatile carrier for aroma chemicals, such that it does not distort subtle fragrance. Diisopropyl Adipate ester is valued for its rapid absorbency and low residual tack. Other usages include sun care, deodorants, lipsticks, hand lotions and men's grooming aids. In an alternative embodiment that also comprises Inaja oil, phospholipids are not included, as shown in Table 6 below.

TABLE 6

Ingredients of an Exemplary Composition

| Raw Material/<br>Trade Name | INCI Name | Optimal<br>Concentration | Range<br>Concentration |
| --- | --- | --- | --- |
| Pracaxi Oil | *Pentaclethra Macroloba* Seed Oil | 20% | 10 to 50% |
| Patauá Oil | *Oenocarpus Bataua* Fruit Oil | 30% | 15 to 40% |
| Inaja Oil | *Maximiliana Maripa* Seed Oil | 25% | 10 to 30% |
| Ceraphyl 230 | Diisopropyl Adipate | 25% | 10 to 30% |

In the embodiment above and similar to that described above with respect to the exemplary formulation of Table 5, the ingredients in Table 6 may be mixed at about 50 degrees Celsius until there is a uniform consistency. The mixture is then homogenized to reduce particle sizes by way of a rotor stator or high pressure homogenization, as further described herein. This composition listed in Table 6 does not include any phospholipids, butters, or skin lipids.

Example 1

Figure 2:
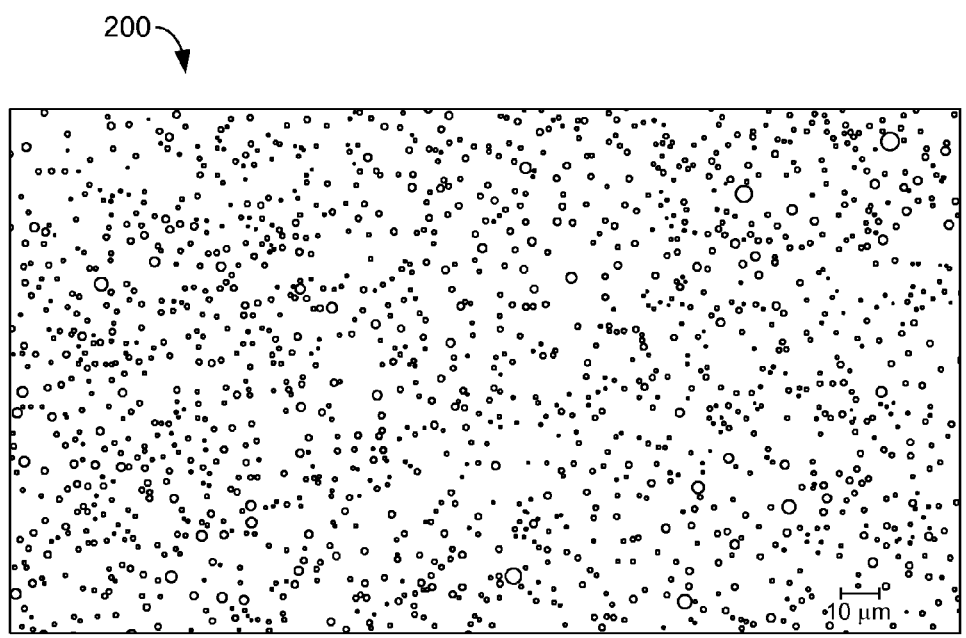
FIG. 2 illustrates a microscopy picture showing the distribution of liposome particle sizes, in accordance with an embodiment of the present invention.

In order to test particle size of the composition, a particle size analysis was conducted on a Malvern MasterSizer diffractor. When the composition was produced, 90% of the solution had a particle size of around 9 microns. This is clearly shown in FIG. 1. FIG. 1 is a logarithmic graph 100 that illustrates the particle size distribution, and shows volume, in percent, on the "y" axis and the particle size in microns (μm) on the "x" axis. As mentioned, while compositions used for permeation enhancements are typically more in the range of 10-100 microns, the liposomes of the composition described herein are in the range of 5-20 microns. In some embodiments, a small percentage of the liposomes have particle sizes greater than 20 microns, but still less than 100 microns, or even 80 microns. FIG. 2 is a microscopy picture 200 of the lipoderm core showing the distribution of liposome particle sizes.

Example 2

While there are various methods to produce the composition disclosed herein, such as the embodiment listed above, not all of these methods will be disclosed herein for the sake of brevity. For exemplary purposes only, the penetration enhancement composition may be produced in the amount of 500 gm. Initially, Pracaxi oil is added to a vessel, along with Plukenetia volubilis seed oil and Phosal 75 SA, whose components are listed above. If Phosal 75 SA is not used, its components may be individually added to the vessel. The mixture of these components is headed to about 60° C., with slow mixing at a mixing speed of around 500 RPM. The heat is then stopped and the mixing speed is increased to 1000 RPM. In another vessel, water and DMS 3015, whose components are listed above, are mixed until congealed. The contents of the two vessels are mixed together and mixed at a mixing speed of about 4000 RPM for approximately two minutes. The mixing is then stopped such that the composition can be packaged in the appropriate containers.

Example 3

Another example is provided to produce about 100 kg of the penetration enhancement composition using a high pressure production method. Here, water and DMS 3015 are added to a first vessel. These components are mixed in the first vessel at a mixing speed of about 5000 RPM for about five minutes. In a second vessel, Pracaxi oil, Plukenetia volubilis seed oil, and Phosal 75 SA are mixed together until there is a clear solution. After about five minutes of mixing, the mixing is stopped. The mixture in the second vessel is added to the mixture in the first vessel. These are mixed together for about ten minutes at a mixing speed of about 5000 RPM. Using a vacuum system, the pressure is decreased to about negative 2.5 bars for about five minutes. Air is discarded from the vacuum and the composition is pumped out using the dispersing outlet of the vessel.

Example 4

In order to illustrate the ability of the composition described herein to function as a permeation enhancer, in-vitro ex-vivo (human skin) testing was performed using the Franz diffusion cell method. The active ingredient, here a drug, is ketoprofen, a commonly used non-steroidal anti-inflammatory drug (NSAID) with analgesic and antipyretic effects. It generally acts by inhibiting the body's production of prostaglandin. Ketoprofem may be offered as a gel for topical application. When tested, the concentration of the permeation enhancement composition was about 5% w/w. The concentration of the ketoprofen used in the study was about 10% w/w. Table 6 below illustrates the various other components of the composition, other than ketoprofen.

TABLE 6

Components of composition when used with an active ingredient, ketoprofen

| | % w/w |
| --- | --- |
| PHASE A | |
| Phenoxyethanol | 0.55 |
| Glycerin USP | 2 |
| Purified Water | 68 |
| Edetate Disodium Dihydrate | 0.2 |
| PHASE B | |
| Stearyl Alcohol NF | 2 |
| Cetearyl Alcohol and Ceteareth-20 | 4.5 |
| Dow Corning 200 (350 CST) (Dimethicone) | 1 |
| Isopropyl Myristate NF | 5.5 |
| Cetyl Alcohol | 2.3 |
| Butylated hydroxytoluene (BHT) | 0.25 |
| Wheat Germ oil 2.0 Iu/G min | 3 |
| Magnesium Aluminium Silicate NF | 0.035 |
| Xanthan Gum | 0.035 |
| Caprylic/Capric Triglycerides | 1 |
| PHASE C | |
| The Composition | 5 |
| Purified water | 5 |
| PHASE D | |
| SEPIGEL 305 (Polyacrylamide/C13-14 Isoparaffin/Laureth-7) | 1 |

TABLE 6-continued

Components of composition when used with an active ingredient, ketoprofen

| | % w/w |
|---|---|
| PHASE E | |
| Methylchloroisothiazolinone/ Methylisothiazolinone | 0.035 |
| Purified water | 1 |

Figure 3:
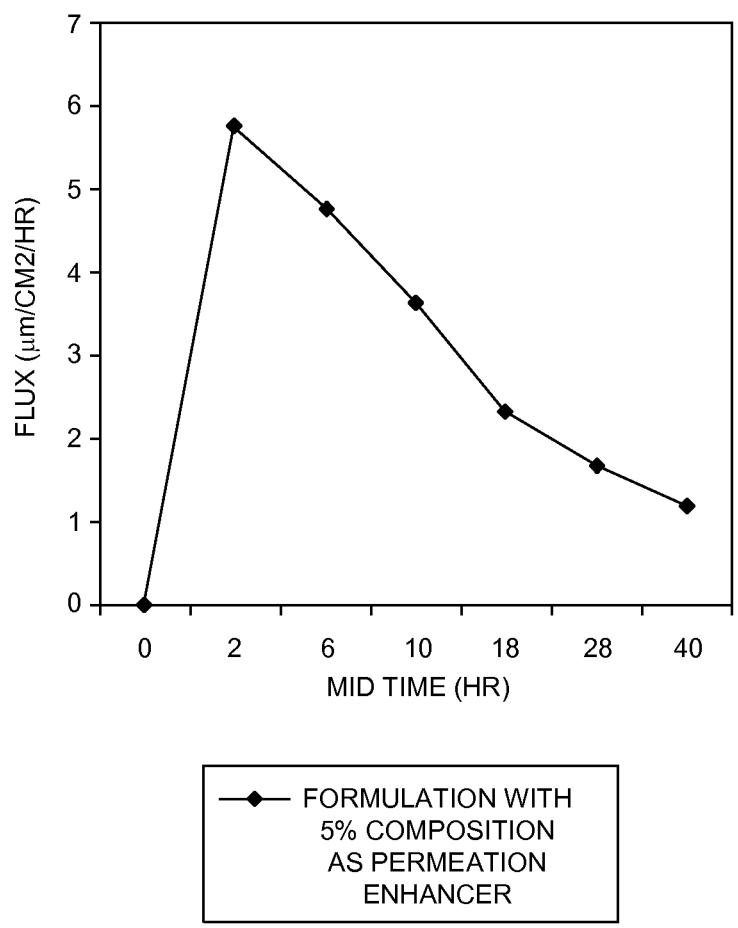
FIG. 3 illustrates mean flux over time for an exemplary formulation, in accordance with an embodiment of the present invention.

In FIG. 3, is a graph 300 that illustrates the percutaneous flux rate results. The mean flux in µg/cm$^2$/hour is shown on the "y" axis and the mid time in hours is shown on the "x" axis. The illustrated line represents the formulation with 5% of the composition being the permeation enhancer. As shown, the flux is highest at around 2 hours. Steady-state flux (mass/time or mass/area/time) is determined from the slope of the linear portion of the cumulative chemical absorbed versus the time plot. Comparing these fluxes across a range of pharmaceutical products with exactly the same method allows acceptable rank-ordering of compounds for their ability to penetrate skin, which can be useful for selection of compounds or development of formulations.

Figure 4:
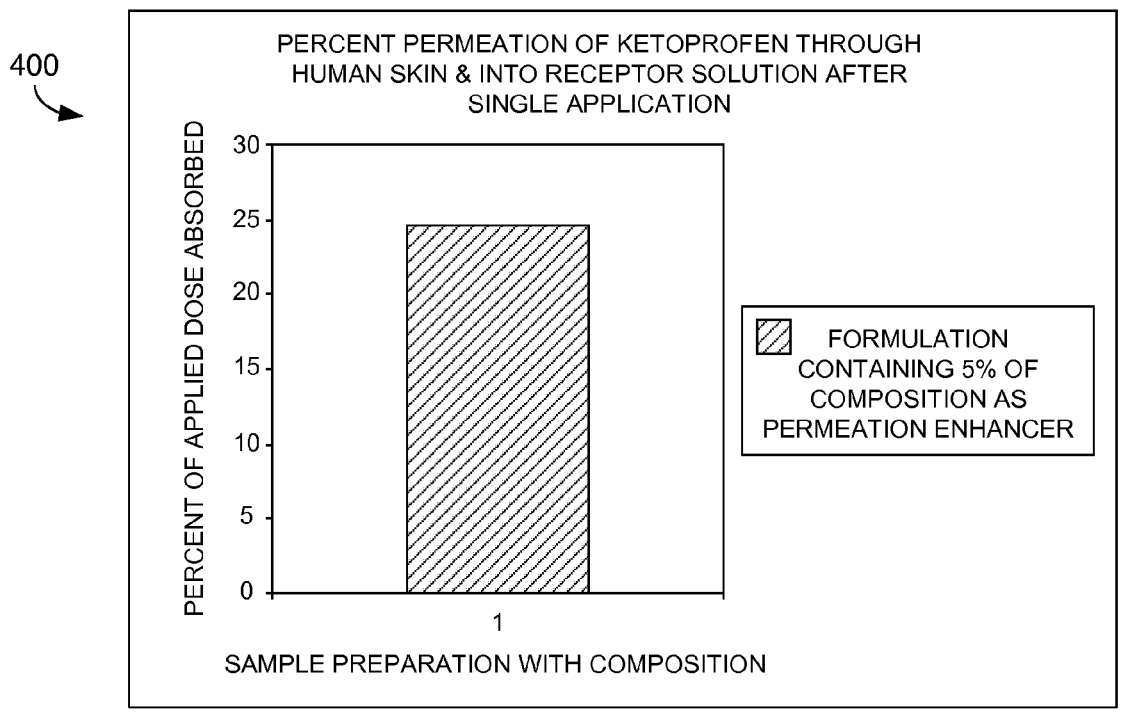
FIG. 4 illustrates the percent of the applied dose of an exemplary formulation absorbed, in accordance with an embodiment of the present invention.

FIG. 4 is a graph 400 that illustrates the amount (in percent) of permeation of ketoprofen through human skin when using the permeation enhancement composition described herein. About 24.6% is absorbed into the skin when using the permeation enhancement composition.

Figure 5:
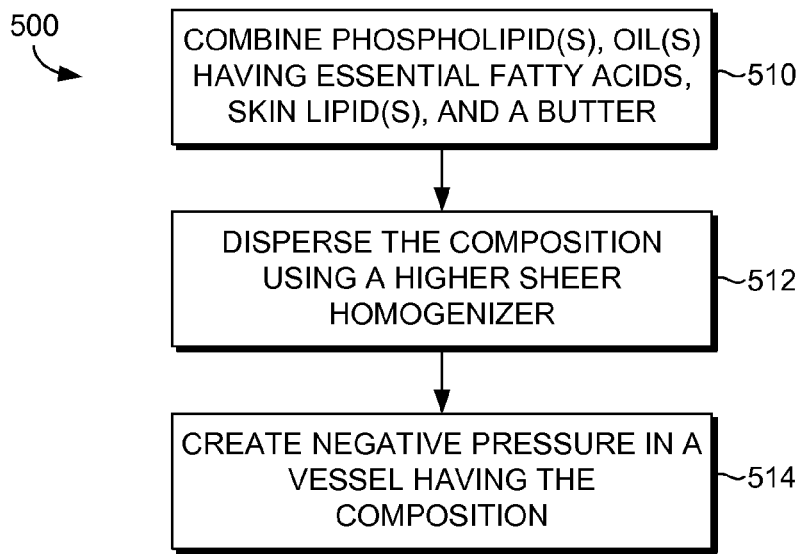
FIG. 5 illustrates a method for preparing a natural composition to be used for skin permeation, in accordance with an embodiment of the present invention.

FIG. 5 illustrates a flow diagram of a method 500 for preparing a natural composition to be used for skin permeation, in accordance with an embodiment of the present invention. At step 510, various components are combined to form a natural composition. These components include one or more phospholipids, one or more oils having essential fatty acids, behenic acid, and oleic acid, one or more skin lipids, and a butter having linoleic acid and linolenic acid. One of the oils, in one embodiment, is Pracaxi oil. At step 512, the composition is dispersed in a vessel using a high shear homogenizer. The composition may be mixed in different batches and then all bathes may be mixed together. Mixing rates may vary, and may include speeds of 1000 RPM, 5000 RPM, etc. As mentioned, a high shear homogenizer may be used for the dispersing of the composition. At step 514, negative pressure is created in the vessel having the composition. In one embodiment, the pressure reaches about negative 2.5 bars, although this pressure may vary. The negative pressure, in one embodiment, is created by a vacuum system. The methods presented herein may allow for the size of the liposomes to reach the range of 5-20 microns, which allows for more stable particles and better skin permeation than larger particle sizes.

Figure 6:
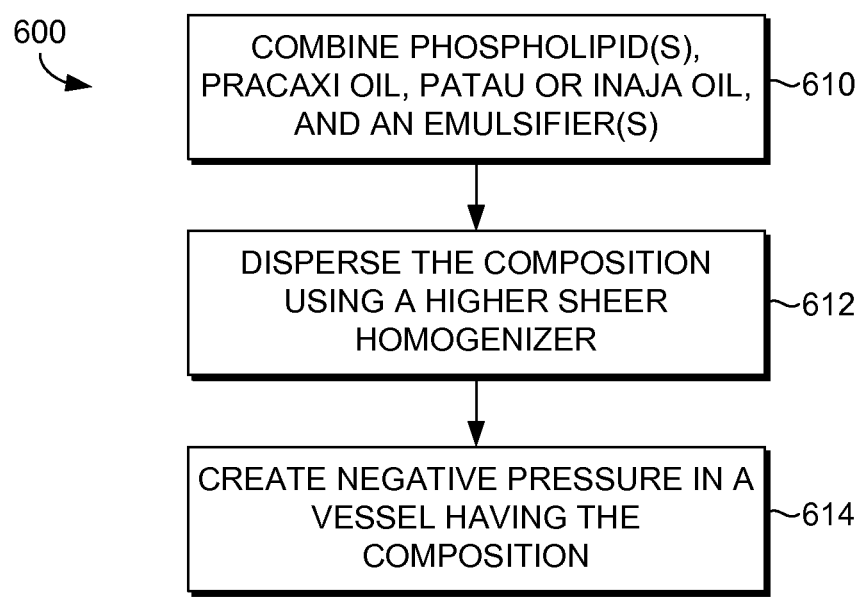
FIG. 6 illustrates another method for preparing a natural composition to be used for skin permeation, in accordance with an embodiment of the present invention.

Turning now to FIG. 6, a flow diagram is illustrated of a method 600 for preparing a natural composition to be used for skin permeation, in accordance with an embodiment of the present invention. At step 610, a phospholipid(s), Pracaxi oil, Patauá oil or Inaja oil, and an emulsifier are combined. At step 612, the composition is dispersed in a vessel using a high shear homogenizer. The composition may be mixed in different batches and then all bathes may be mixed together. Mixing rates may vary, and may include speeds of 1000 RPM, 5000 RPM, etc. As mentioned, a high shear homogenizer may be used for the dispersing of the composition. At step 614, negative pressure is created in the vessel having the composition. In one embodiment, the pressure reaches about negative 2.5 bars, although this pressure may vary. The negative pressure, in one embodiment, is created by a vacuum system. The methods presented herein may allow for the size of the liposomes to reach the range of 5-20 microns, which allows for more stable particles and better skin permeation than larger particle sizes.

The present invention has been described in relation to particular embodiments, which are intended in all respects to be illustrative rather than restrictive. Since many possible embodiments may be made of the invention without departing from the scope thereof, it is to be understood that all matter herein set forth is to be interpreted as illustrative and not in a limiting sense. Alternative embodiments will become apparent to those of ordinary skill in the art to which the present invention pertains without departing from its scope.

From the foregoing, it will be seen that this invention is one well adapted to attain all the ends and objects set forth above. It will be understood that certain features and subcombinations are of utility and may be employed without reference to other features and subcombinations. This is contemplated and within the scope of the claims.

The invention claimed is:

1. A natural liposomal composition to be used for skin permeation, the composition comprising a combination of:
   10-50% w/w of Pracaxi oil;
   15-40% w/w of Patauá oil;
   10-30% w/w of Inaja oil, wherein Pracaxi oil, Patauá oil, and Inaja oil are used as permeation enhancers in the natural composition to decrease irritation, provide hydration, and restore a cutaneous permeability of skin, the Pracaxi oil comprising about 20% behenic acid and about 35% oleic acid;
   10-30% w/w of one or more emollients; and
   10-90% w/w of purified water,
   wherein a substantial portion of liposomes of the natural liposomal composition are about 5-20 microns.

2. A natural liposomal composition of claim 1, wherein the natural composition does not include any phospholipids.

3. A natural liposomal composition of claim 1, wherein 20% w/w of Pracaxi oil, 30% of Patauá oil, and 25% of Inaja oil is used in the natural composition.

4. A natural liposomal composition of claim 1, wherein each of the Pracaxi oil, the Patauá oil, and the Inaja oil comprise one or more of lauric acid, oleic acid, and behenic acid.

5. A natural liposomal composition of claim 1, wherein the composition is added to a product having at least one active ingredient to provide permeation enhancement to the product.

6. A natural liposomal composition of claim 1, wherein the addition of the Pracaxi oil, the Patauá oil, and the Inaja oil provides less irritation to skin than the lauric acid, the behenic acid, and the oleic acid without the Pracaxi oil, the Pataua oil, and the Inaja oil.

7. A natural liposomal composition of claim 6, wherein use of the Pracaxi oil, the Patauá oil, and the Inaja oil is less irritating to the skin because of anti-inflammatory properties of the essential fatty acids in the Pracaxi oil, the Patauá oil, and the Inaja oil.

8. The natural liposomal composition of claim 1, further comprising one or more of:
   10-40% w/w of one or more phospholipids; or
   5-30% w/w of one or more emollients or solubilizers.

9. The natural liposomal composition of claim 8, wherein the one or more phospholipids include an unsaturated phospholipid and a hydrogenated phospholipid.

10. The natural liposomal composition of claim 8, the one or more phospholipids include one or more of phosphatidylcholine, lysophosphotidylcholine, a hydrogenated phospholipid, or an unsaturated phospholipid.

11. The natural liposomal composition of claim 8, wherein the composition is added to a product having at least one active ingredient to provide permeation enhancement to the product.

12. The natural liposomal composition of claim 8, wherein the Pracaxi oil, the Patauá oil, and the Inaja oil contain lauric acid, behenic acid, and oleic acid that are permeation enhancers, wherein the use of the Pracaxi oil, the Patauá oil, and the Inaja oil are less irritating to the skin than the lauric acid, the behenic acid, and the oleic acid when used alone.

* * * * *